(12) United States Patent
Pianca (10) Patent No.: US 8,774,941 B2
(45) Date of Patent: Jul. 8, 2014

(54) SYSTEMS AND METHODS FOR MAKING AND USING PADDLE LEAD ASSEMBLIES FOR ELECTRICAL STIMULATION SYSTEMS

(75) Inventor: Anne Margaret Pianca, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/224,681

(22) Filed: Sep. 2, 2011

(65) Prior Publication Data

US 2012/0071952 A1 Mar. 22, 2012

Related U.S. Application Data

(60) Provisional application No. 61/383,634, filed on Sep. 16, 2010.

(51) Int. Cl.
*A61N 1/372* (2006.01)

(52) U.S. Cl.
USPC .......................................................... 607/117

(58) Field of Classification Search
USPC .................................. 607/116–17, 148, 152
See application file for complete search history.

(56) References Cited

U.S. PATENT DOCUMENTS

| | | | |
|---|---|---|---|
| 5,417,719 A | 5/1995 | Hull | |
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 7,244,150 B1 | 7/2007 | Brase et al. | |
| 7,437,193 B2 | 10/2008 | Parramon et al. | |
| 7,672,734 B2 | 3/2010 | Anderson et al. | |
| 7,761,165 B1 | 7/2010 | He et al. | |
| 7,904,161 B2 * | 3/2011 | Osypka ........................ 607/37 |
| 7,949,395 B2 | 5/2011 | Kuzma | |
| 7,974,706 B2 | 7/2011 | Moffitt et al. | |
| 2005/0165465 A1 | 7/2005 | Pianca et al. | |

(Continued)

FOREIGN PATENT DOCUMENTS

| | | | | |
|---|---|---|---|---|
| WO | 2007087626 A2 | 8/2007 | | |
| WO | WO 2007101999 A2 * | 9/2007 | ............... | A61N 1/05 |
| WO | 2010028084 A2 | 3/2010 | | |

OTHER PUBLICATIONS

International Search Report for International Patent Application No. PCT/US2011/050382 mailed Nov. 30, 2011.

*Primary Examiner* — Amanda Patton
(74) *Attorney, Agent, or Firm* — Lowe Graham Jones PLLC; Patrick R. Turner (57) ABSTRACT

A paddle lead assembly for providing electrical stimulation of patient tissue includes a paddle body. The paddle body includes four columns of electrodes, each column including at least one electrode. The columns include two outer columns flanking two inner columns. The paddle lead assembly further includes a plurality of lead bodies coupled to the paddle body. At least one terminal is disposed on each of the plurality of lead bodies. A plurality of conductive wires couple each of the electrodes to at least one of the plurality of terminals.

18 Claims, 7 Drawing Sheets

(56) References Cited

U.S. PATENT DOCUMENTS

| | | |
|---|---|---|
| 2007/0150036 A1 | 6/2007 | Anderson |
| 2007/0219595 A1 | 9/2007 | He |
| 2008/0071320 A1 | 3/2008 | Brase |
| 2008/0269856 A1* | 10/2008 | Cross et al. .................. 607/116 |
| 2010/0057176 A1* | 3/2010 | Barker ......................... 607/117 |
| 2010/0057177 A1* | 3/2010 | Moffitt et al. ................ 607/117 |
| 2010/0070010 A1 | 3/2010 | Simpson |
| 2010/0137943 A1* | 6/2010 | Zhu ............................... 607/59 |

* cited by examiner

SYSTEMS AND METHODS FOR MAKING AND USING PADDLE LEAD ASSEMBLIES FOR ELECTRICAL STIMULATION SYSTEMS

CROSS-REFERENCE TO RELATED APPLICATIONS

This application claims the benefit under 35 U.S.C. §119(e) of U.S. Provisional Patent Application Ser. No. 61/383,634 filed on Sep. 16, 2010, which is incorporated herein by reference.

FIELD

The present invention is directed to the area of implantable electrical stimulation systems and methods of making and using the systems. The present invention is also directed to implantable paddle leads that include electrodes disposed on paddle bodies and one or more lead bodies coupled to the paddle bodies, as well as methods of making and using the leads, lead bodies, paddle bodies, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a paddle lead assembly for providing electrical stimulation of patient tissue includes a paddle body. The paddle body includes four columns of electrodes, each column including at least one electrode. The columns include two outer columns flanking two inner columns. The paddle lead assembly further includes a plurality of lead bodies coupled to the paddle body. At least one terminal is disposed on each of the plurality of lead bodies. A plurality of conductive wires couple each of the electrodes to at least one of the plurality of terminals.

In another embodiment, an electrical stimulating system includes a paddle body. The paddle body includes four columns of electrodes, each column including at least one electrode. The columns include two outer columns flanking two inner columns. The paddle lead assembly further includes a plurality of lead bodies coupled to the paddle body. At least one terminal is disposed on each of the plurality of lead bodies. A plurality of conductive wires couple each of the electrodes to at least one of the plurality of terminals. The paddle lead assembly additionally includes at least one control module. The at least one control module is configured and arranged to electrically couple to each of the plurality of lead bodies. Each of the at least one control module includes a housing and an electronic subassembly disposed in the housing. A connector is configured and arranged for receiving at least one of the plurality of lead bodies, the connector includes a connector housing defining at least one port at a distal end of the connector The at least one port is configured and arranged for receiving a portion of at least one of the plurality of lead bodies. At least one connector contact is disposed in each of the at least one ports defined by the connector housing. The at least one connector contact is configured and arranged to couple to the at least terminal disposed on each of the plurality of the lead bodies.

In yet another embodiment, a method for implanting a paddle lead includes inserting a paddle lead assembly into a patient, the paddle lead assembly including a paddle body. The paddle body includes four columns of electrodes, each column including at least one electrode. The columns include two outer columns flanking two inner columns. The paddle lead assembly further includes a plurality of lead bodies coupled to the paddle body. At least one terminal is disposed on each of the plurality of lead bodies. A plurality of conductive wires couple each of the electrodes to at least one of the plurality of terminals. The paddle lead assembly additionally includes at least one extension element coupling each of the plurality of lead bodies to the paddle body. A junction couples the at least one extension element to each of the plurality of lead bodies. The plurality of conductive wires extend along the at least one extension element to the junction. The plurality of conductive wires are divided up into a plurality of distinct groupings in the junction. A different one of the groupings of conductive wires extends along each of the plurality of lead bodies. The plurality of lead bodies couple to the junction such that the plurality of lead bodies are arranged into a single layer in a side-by-side configuration that comprises at least one inner lead body flanked by two outer lead bodies. Each of the plurality of lead bodies is coupled to at least one adjacent lead body by at least one weakened region configured and arranged to permit manual separation of the coupled lead bodies. The weakened region between a first proximal element and an adjacent second proximal element is separated such that the terminals of the first proximal element are separated from terminals disposed on the second proximal element. The terminals of the first proximal element are inserted into a connector electrically coupled to an implantable pulse generator.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable paddle leads that include electrodes disposed on paddle bodies and one or more lead bodies coupled to the paddle bodies, as well as methods of making and using the leads, lead bodies, paddle bodies, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; 7,244,150; 7,672,734; 7,761,165; 7,949,395; 7,974,706; and U.S. Patent Applications Publication Nos. 2005/0165465; 2007/0150036; 2007/0219595; and 2008/0071320, all of which are incorporated by reference.

Figure 1:
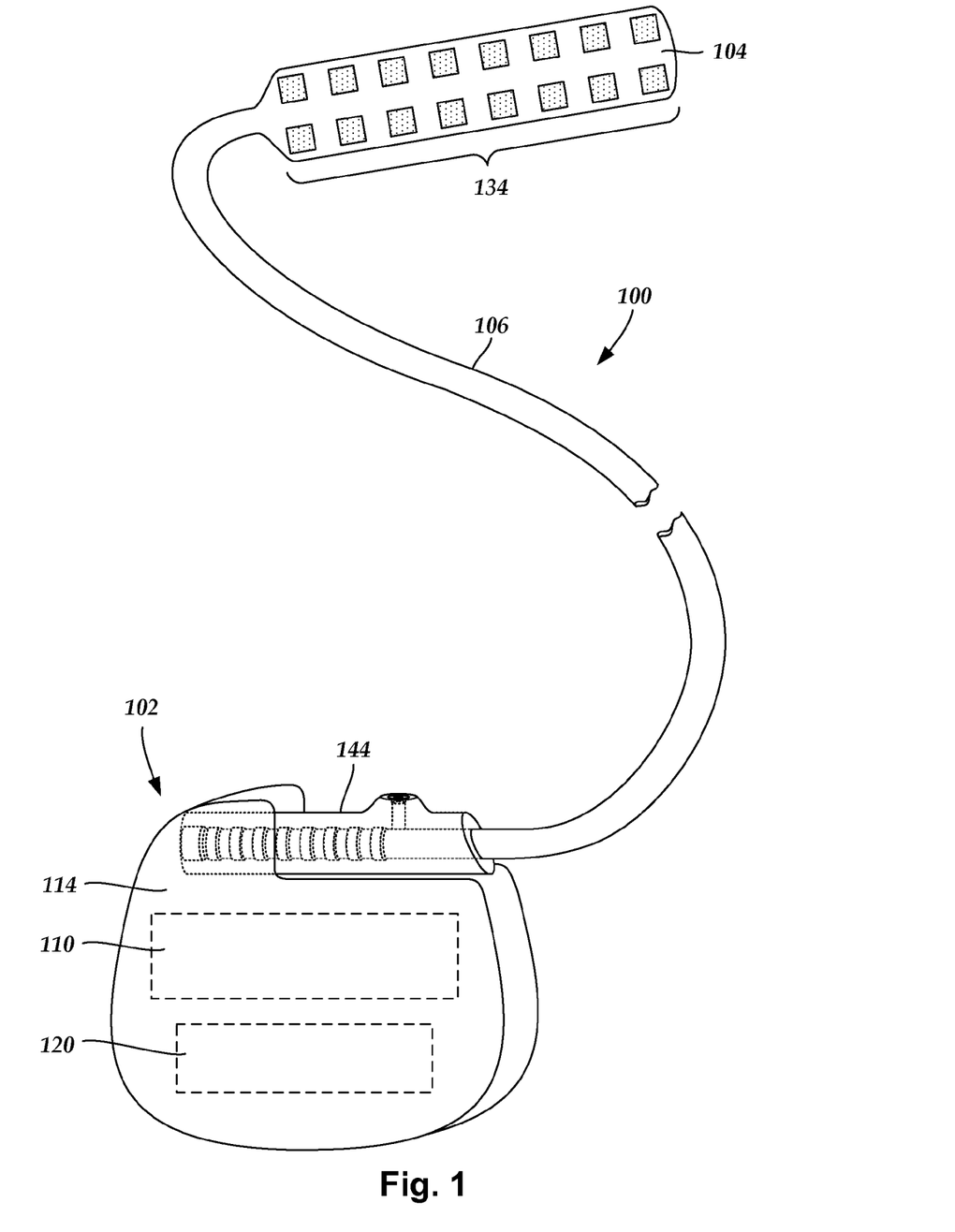
FIG. 1 is a schematic view of one embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144, 201 (FIGS. 2A and 2B, see also 222 and 250 of FIG. 2C) into which the proximal end of the one or more lead bodies 106 can be plugged to make an electrical connection via conductive contacts on the control module 102 and terminals (e.g., 210 in FIGS. 2A and 2B and 236 of FIG. 2C) on each of the one or more lead bodies 106. In addition, one or more lead extensions 212 (see FIG. 2C) can be disposed between the one or more lead bodies 106 and the control module 102 to extend the distance between the one or more lead bodies 106 and the control module 102.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, spinal cord stimulation, brain stimulation, neural stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 210 in FIG. 2A and 236 of FIG. 2C) are typically disposed at the proximal end of the one or more lead bodies 106 for connection to corresponding conductive contacts (e.g., 214 in FIG. 2A and 240 of FIG. 2C) in connectors (e.g., 144 in FIGS. 1-2A and 222 and 250 of FIG. 2C) disposed on, for example, the control module 102 (or to other devices, such as conductive contacts on a lead extension, an operating room cable, a splitter, or an adaptor). Conductive wires (not shown) extend from the terminals (e.g., 210 in FIG. 2A and 236 of FIG. 2C) to the electrodes 134. Typically, one or more electrodes 134 are electrically coupled to a terminal (e.g., 210 in FIG. 2A and 236 of FIG. 2C). In some embodiments, each terminal (e.g., 210 in FIG. 2A and 236 of FIG. 2C) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 2A:
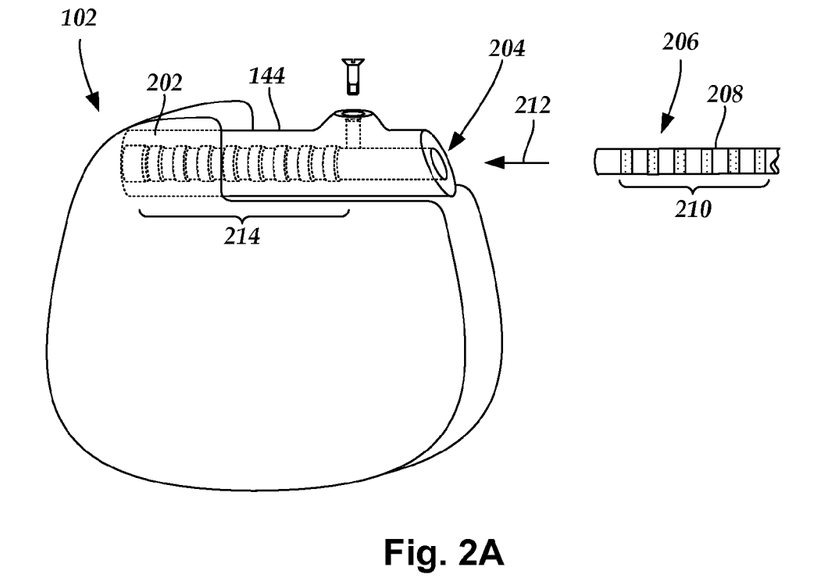
FIG. 2A is a schematic view of one embodiment of a proximal portion of a lead, a connector, and a control module of an electrical stimulation system, according to the invention.
Figure 2B:
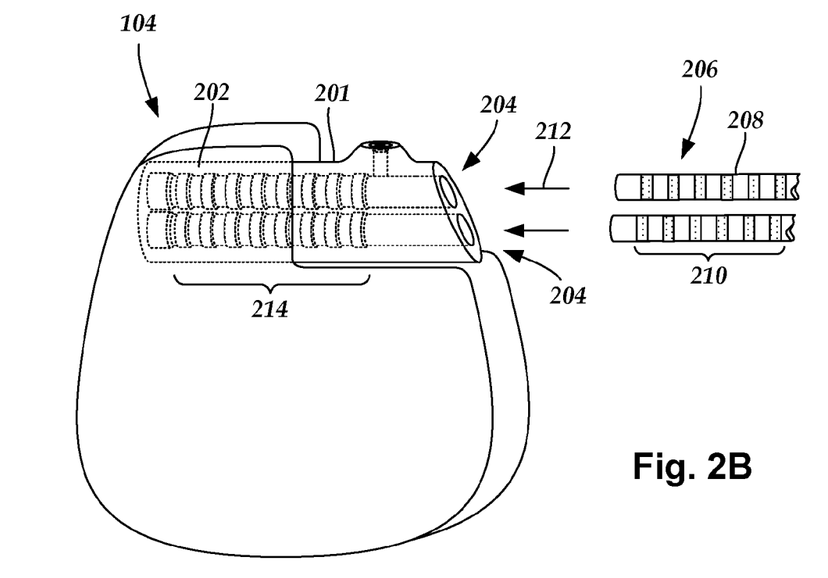
FIG. 2B is a schematic view of another embodiment of a proximal portion of a lead, a connector, and a control module of an electrical stimulation system, according to the invention.

In at least some embodiments, leads are coupled to connectors disposed on control modules. FIG. 2A is a schematic perspective view of one embodiment of the one-port connector 144 disposed on the control module 102. FIG. 2B is a schematic perspective view of one embodiment of a two-port connector 201 disposed on the control module 102. One or more leads 208 are shown configured and arranged for insertion to the control module 102. The connector 144 includes a connector housing 202. The connector housing 202 defines at least one port 204 into which a proximal end 206 of the one or more leads 208 with terminals 210 can be inserted, as shown by directional arrows 212. The connector housing 202 also includes a plurality of conductive contacts 214 within each port 204. When the one or more leads 208 are inserted into the port 204, the conductive contacts 214 can be aligned with the terminals 210 on the lead(s) 208 to electrically couple the control module 102 to the electrodes (134 of FIG. 1) disposed at a distal end of the one or more leads 208. Examples of connectors in control modules are found in, for example, U.S. Pat. No. 7,244,150 and U.S. Patent Application Publication No. 2008/0071320 A1, which are incorporated by reference.

It will be understood that the control module 102 may have any suitable number of ports including, for example, one, two, three, four, five, six, seven, eight, or more ports. It will also be understood that each of the ports can have any number of conductor contacts 214 disposed in the port. For example, in at least some embodiments, the control module has four ports, with eight conductive contacts 214 disposed in each port to define a 32-channel control module, which may be an implantable pulse generator for generating electrical pulses.

Figure 2C:
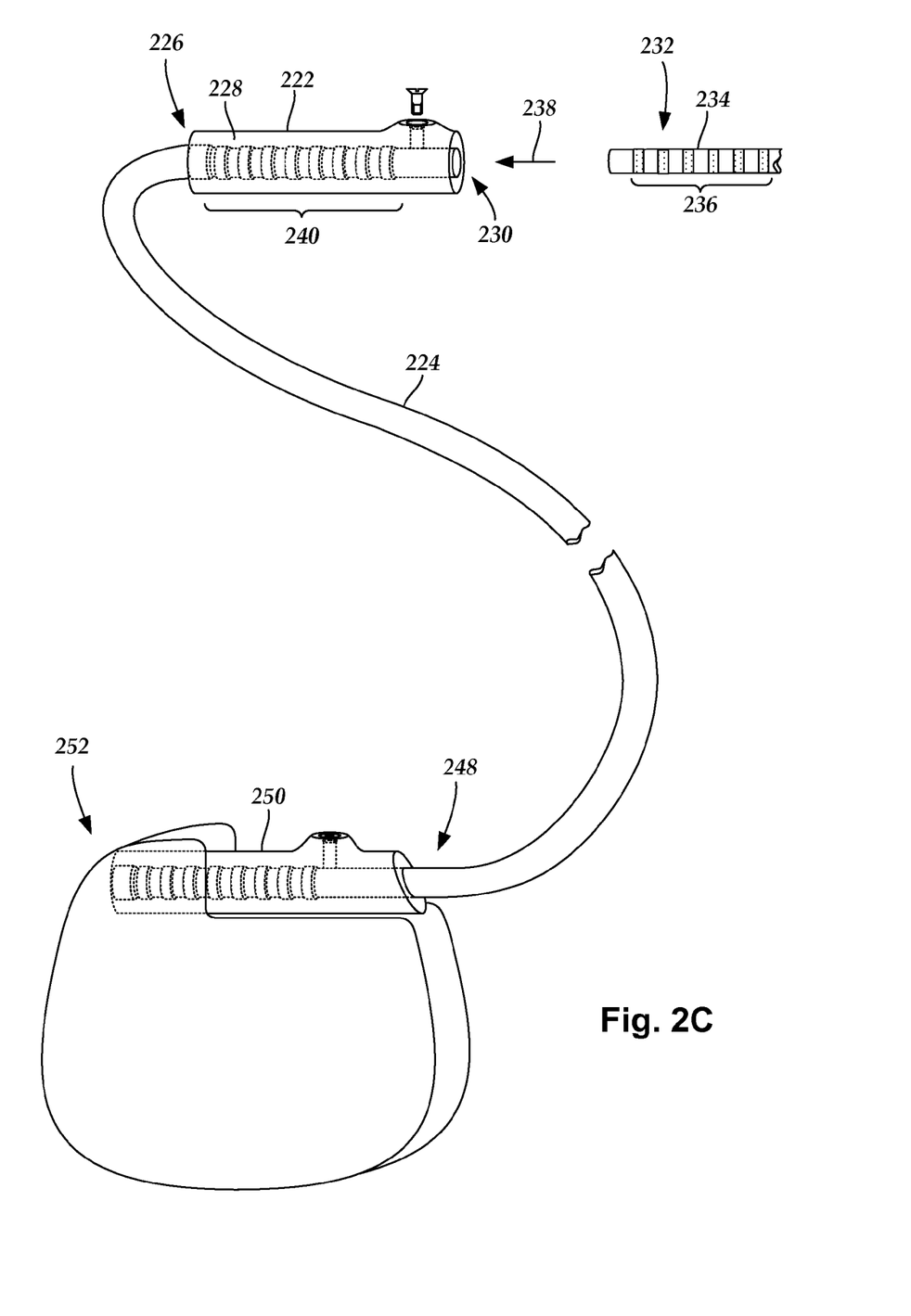
FIG. 2C is a schematic view of one embodiment of a proximal portion of a lead and a lead extension of an electrical stimulation system, according to the invention.

In FIG. 2C, a connector 222 is disposed on a lead extension 224. The connector 222 is shown disposed at a distal end 226 of the lead extension 224. The connector 222 includes a connector housing 228. The connector housing 228 defines at least one port 230 into which a proximal end 232 of a lead 234 with terminals 236 can be inserted, as shown by directional arrow 238. The connector housing 228 also includes a plurality of conductive contacts 240. When the lead 234 is inserted into the port 230, the conductive contacts 240 disposed in the connector housing 228 can be aligned with the terminals 236 on the lead 234 to electrically couple the lead extension 224 to the electrodes (134 of FIG. 1) disposed at a distal end (not shown) of the lead 234.

In at least some embodiments, the proximal end of a lead extension is similarly configured and arranged as a proximal end of a lead. The lead extension 224 may include a plurality of conductive wires (not shown) that electrically couple the conductive contacts 240 to a proximal end 248 of the lead extension 224 that is opposite to the distal end 226. In at least some embodiments, the conductive wires disposed in the lead extension 224 can be electrically coupled to a plurality of terminals (not shown) disposed on the proximal end 248 of the lead extension 224. In at least some embodiments, the proximal end 248 of the lead extension 224 is configured and arranged for insertion into a connector disposed in another lead extension. In other embodiments, the proximal end 248 of the lead extension 224 is configured and arranged for insertion into a connector disposed in a control module. As an example, in FIG. 2C the proximal end 248 of the lead extension 224 is inserted into a connector 250 disposed in a control module 252.

It may be useful to design a lead with more electrodes than the lead illustrated in FIG. 1. For example, a patient may be experiencing pain emanating from an area greater in size than the dimensions of an array of electrodes (e.g., 134 of FIG. 1) disposed on the distal end of a conventional paddle lead. It may also be useful to stimulate two or more sites separately situated along the spinal cord.

One way to increase stimulation coverage is to provide a lead with greater dimensions and either increase the amount of space between adjacent electrodes, or increase the size of one or more of the electrodes. When the amount of space between adjacent electrodes is increased or the size of one or more of the electrodes in increased, however, linear electrode density may decrease to a sub-therapeutic level.

Another way to increase stimulation coverage is to provide a lead with the same or larger dimensions and increase the number of electrodes on the lead. A lead with additional electrodes, however, may also employ an increased number of conductive wires to electrically couple the electrodes to one or more pulse generators.

Regardless of how many conductive wires are disposed on a paddle lead, the paddle lead is typically configured and arranged to couple to one or more connectors (e.g., on a control module, a lead extension, or the like). It may, therefore, be an advantage to form leads to be compatible with conventional connectors. At least some conventional connectors include either one port or two ports that are each configured and arranged with eight conductive contacts to receive eight conductive wires (see e.g., 144 of FIG. 2A and 201 of FIG. 2B). Thus, for example, when a paddle lead includes sixteen electrodes, the conductive wires electrically coupled to the electrodes may be divided into two lead bodies, with eight conductive wires disposed in each lead body. When eight of the sixteen conductive wires are disposed in each lead body, then each of the lead bodies can be input into a different port of a two-port connector of, for example, a control module or a lead extension.

A paddle lead can include any number of electrodes including, for example, one, two, three, four, five, six, seven, eight, nine, ten, eleven, twelve, thirteen, fourteen, fifteen, sixteen, eighteen, twenty, twenty-two, twenty-four, twenty-six, twenty-eight, thirty, thirty-two, thirty-four, thirty-six, thirty-eight, forty, forty-two, forty-four, forty-six, forty-eight, fifty, fifty-two, fifty-four, fifty-six, fifty-eight, sixty-sixty-two, sixty-four, or more electrodes. It will be understood that other numbers of electrodes may be used instead. It may be an advantage to form leads having numbers of electrodes that are multiples of eight in order to couple to each conductive contact of a conventional one-port connector having eight conductive contacts. It may also be an advantage to form leads having numbers of electrodes that are multiples of sixteen in order to couple to each contact of a conventional two-port connector having sixteen conductive contacts.

In at least some embodiments, the electrodes disposed on the paddle lead are arranged into columns. The electrodes can be arranged into any number of columns including, for example, four, five, six, seven, eight, or more columns. In at least some embodiments, each of the four columns includes eight electrodes. It will be understood that other numbers of electrodes, either fewer or greater, may be disposed in each column. For example, at least one of the columns may include one, two, three, four, five, six, seven, eight, nine, ten, eleven, twelve, thirteen, fourteen, fifteen, sixteen, seventeen, eighteen, nineteen, twenty, or more electrodes.

When a lead includes a plurality of lead bodies, it may be an advantage to form the lead such that each column of electrodes correlates with a different lead body (and, in turn, with terminals disposed on those lead bodies) to improve control of stimulation. For example, for a four-column paddle lead with four lead bodies, it may be an advantage for each of the conductive wires coupled to the electrodes of a first column to be disposed in a first lead body and each of the conductive wires coupled to the electrodes of a second column to be disposed in a second lead body, and so on. As another example, for a four-column paddle lead with four lead bodies, it may be an advantage for each of the conductive wires coupled to the electrodes of outer columns to be disposed in corresponding outer lead bodies, and each of the conductive wires coupled to electrodes of inner columns to be disposed in corresponding inner lead bodies.

It may further be an advantage to correlate individual electrodes of a given column of electrodes with individual terminals disposed along a given lead body. For example, it may be an advantage for conductive wires to couple a proximal-most electrode of a given column of electrodes to a proximal-most terminal disposed along a given lead body, and to couple a distal-most electrode of the given column of electrodes to a distal-most terminal disposed along the given lead body. It may additionally be an advantage to, likewise, consecutively couple any intervening electrodes of the given column of electrodes to any intervening terminals disposed along the given lead body. Alternatively, it may be an advantage for conductive wires to couple a proximal-most electrode of a given column of electrodes to a distal-most terminal disposed on a given lead body, and to couple a distal-most electrode of the given column of electrodes to a proximal-most terminal disposed in the given lead body.

The paddle lead can be configured and arranged for insertion into one or more connectors in many different ways. In at least some embodiments, conductive wires extending from electrodes disposed on the paddle body can be arranged into a plurality of distinct groupings, and each grouping disposed in a different one of a plurality of lead bodies. In at least some embodiments, each of the lead bodies is configured and arranged for direct insertion into the one or more connectors. In at least some embodiments, each of the lead bodies is configured and arranged for insertion into a splitter which, in turn, is configured and arranged for insertion into the one or more connectors. In at least some embodiments, conductive wires extend from the paddle body to an extension element that, in turn, is coupled to the lead bodies.

Figure 3A:
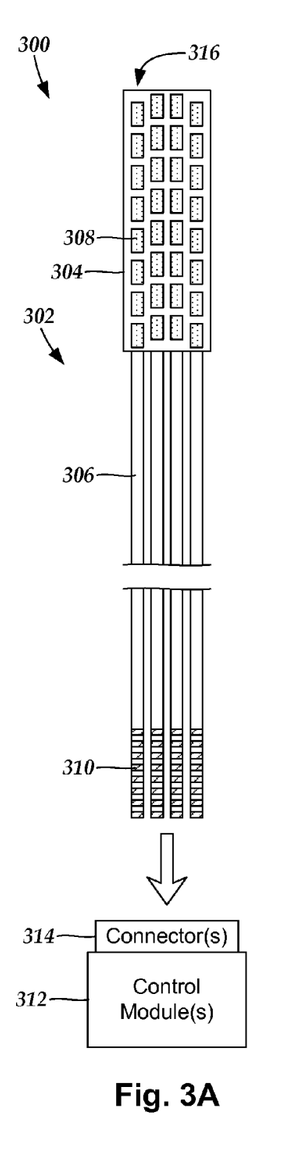
FIG. 3A is a schematic view of one embodiment of a paddle lead assembly of an electrical stimulation system, according to the invention.

FIG. 3A is a schematic view of one embodiment of an electrical stimulation system 300. The electrical stimulation system 300 includes a paddle lead assembly 302. The paddle lead assembly 302 includes a paddle body 304 and lead bodies 306. An array of electrodes 308 is disposed on the paddle body 304. An array of terminals 310 is disposed on each of the lead bodies 306. The electrical stimulation system 300 also includes one or more control modules 312 and one or more connectors 314 for coupling the lead bodies 306 to the control module(s) 312. The terminals 310 are insertable into the one or more connectors 314 such that conductive wires within the lead bodies 306 electrically couple to conductive contacts disposed within one or more ports of the one or more connectors 314.

One or more conductive wires electrically couple the electrodes 308 to the terminals 310. At least a portion of the conductive wires extend within the lead bodies 306. In at least some embodiments, each electrode 308 is coupled to a single different corresponding terminal 310 on one of the lead bodies 306 via a single conductive wire. In at least some embodiments, at least one conductive wire extends along each of the lead bodies 306.

In at least some embodiments, the electrodes 308 are arranged into columns 316. In at least some embodiments, each different column 316 of electrodes is electrically coupled to terminals disposed on a different one of the lead bodies 306. In at least some embodiments, the paddle body 304 includes four columns 316 of electrodes. In at least some embodiments, each column 316 includes eight electrodes. In at least some embodiments, each of the lead bodies 306 are the same length. In at least some embodiments, at least one of the lead bodies 306 has a length that is different from at least one other of the lead bodies 306. In at least some embodiments, each of the lead bodies 306 has a different length.

When multiple lead bodies are inserted into a patient, it may be difficult for a medical practitioner to identify which proximal end of which lead body corresponds to which electrode(s). Accordingly, it may be an advantage to provide one or more lead body identification arrangements to facilitate electrode identification. In at least some embodiments, the one or more lead body identification arrangements provide a distinct (e.g., visually, texturally, or the like or combinations thereof) component to one or more of the lead bodies to distinguish one or more of the lead bodies from one or more of the remaining lead bodies. For example, the lead bodies 306 can be formed with different lengths to distinguish (e.g., visually distinguish) each individual lead body 306 from the other lead bodies 306, thereby facilitating identification of which lead bodies include conductive wires coupled to which electrodes. These considerations and arrangements also apply equally to each of the below-described embodiments of the electrical stimulation system.

It will be understood that other lead body identification arrangements may be used in addition to, or in lieu of, the above-mentioned arrangement to facilitate electrode identification. For example, in at least some embodiments, one or more distinct (e.g., visually, texturally, or the like or combinations thereof) markers (e.g., ablated regions, insulated regions, colored regions, rings, bands, or the like or combinations thereof) can be disposed in or on the proximal end of one or more of the lead bodies 306 to distinguish between the lead bodies 306 (e.g., one ring, two rings, three rings, and four rings to indicate electrode column 1, 2, 3, and 4, respectively, or the like).

Any number of lead bodies 306 can be disposed on the paddle lead assembly 302 including, for example, two, three, four, five, six, seven, eight, nine, ten, or more lead bodies 306. In at least some embodiments, the number of lead bodies 306 is equal to the number of columns 316 of electrodes.

Figure 3B:
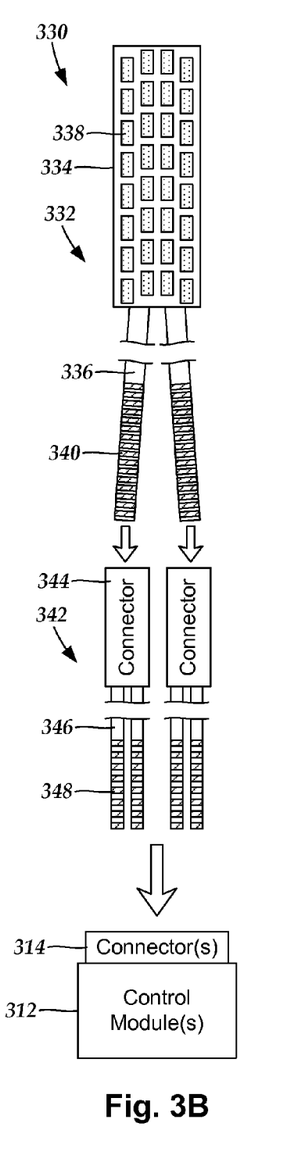
FIG. 3B is a schematic view of a second embodiment of a paddle lead assembly of an electrical stimulation system, according to the invention.

Turning now to FIG. 3B, sometimes a lead body is incompatible with a connector. For example, a lead body may include a number of terminals that exceeds a number of conductor contacts disposed in a connector. In at least some embodiments, a paddle lead assembly may include one or more lead splitters that receive lead bodies and split the conductive wires of the received lead bodies into two or more groupings disposed in splitter bodies that are compatible with, for example, conventional connectors.

FIG. 3B is a schematic view of a second embodiment of an electrical stimulation system 330. The electrical stimulation system 330 includes a paddle lead assembly 332. The paddle lead assembly 332 includes a paddle body 334 and lead bodies 336. An array of electrodes 338 is disposed on the paddle body 334. An array of terminals 340 is disposed on each of the lead bodies 336. The electrical stimulation system 330 also includes lead splitters 342. The lead splitters 342 include connectors 344 and splitter lead bodies 346. Splitter terminal arrays 348 are disposed on the splitter lead bodies 346. The electrical stimulation system 330 also includes the one or more control modules 312 and the one or more connectors 314 for coupling the splitter lead bodies 346 to the control module(s) 312.

Conductive wires (not shown) extending within the lead splitters 342 electrically couple connector contacts within the splitter connectors 344 to terminals of the splitter terminal arrays 348. The splitter conductive wires are split into multiple groupings of conductive wires. Each grouping of conductive wires extends within a different splitter lead body 346. For example, in at least some embodiments, the lead bodies 336 each have sixteen terminals 340 and the splitter terminal arrays 348 each have eight terminals. Thus, in at least some embodiments, a thirty-two electrode paddle lead 332 may be coupled to two lead bodies 336 each having sixteen terminals 340, and each of two lead splitters 342 may receive one of the sixteen-terminal lead bodies 336 and couple the sixteen terminals 340 of the received lead body 336 to two splitter terminal arrays 348 each having eight terminals and each configured and arranged for insertion into the one or more connectors 314 such that conductive wires within the splitter lead bodies 346 electrically couple to conductive contacts disposed within one or more ports of the one or more connectors 314.

FIG. 3B shows the lead splitter 342 that includes two splitter lead bodies 346. It will be understood that the lead splitter 342 may include any number of splitter lead bodies 346 including, for example, three, four, five, six, seven, eight, nine, ten, or more splitter lead bodies 346. Splitter terminals 348 may be disposed on all, or a portion, of the splitter lead bodies 346.

In at least some embodiments, at least one of the splitter lead bodies 346 has a length that is different from at least one other of the splitter lead bodies 346. As discussed above, when multiple lead bodies and lead splitters are inserted into a patient, it may be difficult for a medical practitioner to identify which proximal end of which splitter body corresponds to which electrode(s). Thus, it may be an advantage to form the splitter lead bodies 346 with different lengths to distinguish each splitter lead body 346 from the other splitter lead bodies 346, thereby facilitating identification of which splitter lead body 346 includes conductive wires coupled to which electrodes. It may also be an advantage to incorporate one or more visually distinct markers on one or more of the splitter lead bodies 346, as discussed above with reference to the paddle lead assembly 302 and shown in FIG. 3A.

Figure 3C:
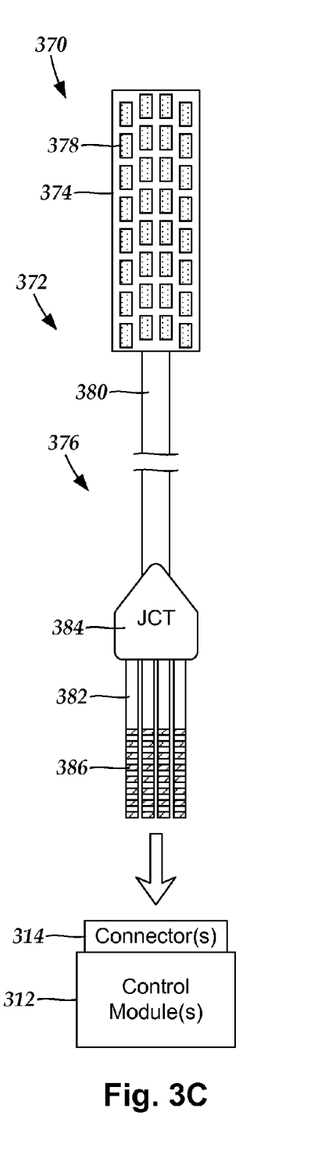
FIG. 3C is a schematic view of a third embodiment of a paddle lead assembly of an electrical stimulation system, according to the invention.

Turning now to FIG. 3C, in at least some embodiments the lead includes a lead body arrangement 376. The lead body arrangement 376 includes an extension element 380 and a plurality of lead bodies 382 disposed proximally to the extension element 380. In at least some embodiments, the extension element 380 is coupled to the lead bodies 382 via one or more junctions 384.

Conductive wires extending within the extension element are divided at the junction into multiple distinct groupings of conductive wires. Each distinct grouping of conductive wires extends within a different proximal element. At least one of the lead bodies is configured and arranged to couple to a connector such that conductive wires within the lead body electrically couple to connector contacts disposed within one or more ports of the connector.

FIG. 3C is a schematic view of a third embodiment of an electrical stimulation system 370. The electrical stimulation system 370 includes a paddle lead assembly 372. The paddle lead assembly 372 includes a paddle body 374 and a lead body arrangement 376. An array of electrodes 378 is disposed on the paddle body 374. The lead body arrangement 376 includes an extension element 380 coupled to the paddle body 374, a plurality of lead bodies 382, and a junction 384 coupling the extension element 380 to the plurality of lead bodies 382. An array of terminals 386 is disposed on at least one of the plurality of lead bodies 382. The electrical stimulation system 370 also includes the one or more control modules 312 and the one or more connectors 314 for coupling the proximal lead bodies 382 to the control module(s) 312.

In at least some embodiments, the extension element 380 has a length that is substantially greater than a length of each of the lead bodies 382. In at least some embodiments, at least one of the lead bodies 382 has a length that is different than at least one other of the lead bodies 382. When multiple lead bodies and junctions are inserted into a patient, it may be difficult for a medical practitioner to identify which proximal end of which lead body corresponds to which electrode(s). Thus, it may be an advantage to form the lead bodies 382 with different lengths to distinguish each of the lead bodies 382 from one another, thereby facilitating identification of which lead body 382 includes conductive wires coupled to which electrodes.

It may be an advantage to use a paddle lead assembly having a single extension element extending from the paddle body 374 because using a single extension element may reduce patient discomfort during insertion or during the implantation period of the electrical stimulation system 370. When multiple lead bodies are inserted into a patient such that each of the lead bodies extends the entire distance between the paddle body and the control module, multiple tunnels may be bored through patient tissue. Each tunnel may cause patient discomfort or lead to potential complications during implantation. Additionally, in order to maintain precise positioning of paddle bodies during operation, some lead bodies may be anchored to patient tissue. Each anchoring may also cause patient discomfort or lead to potential complications during implantation. It may, therefore, be an advantage to only anchor a single extension element to patient tissue in proximity to the paddle body instead of anchoring a plurality of lead bodies.

In at least some embodiments, the transverse profile of the extension element may be reduced to further reduce patient discomfort. In at least some embodiments, the extension element is formed from a single extrusion of one or more polymers (e.g., ethylene tetrafluoroethylene, perfluoroalkoxy, or the like) coated with one or more layers of biocompatible, biostable insulating material (e.g., polyurethane, silicone, or the like).

Figure 4A:
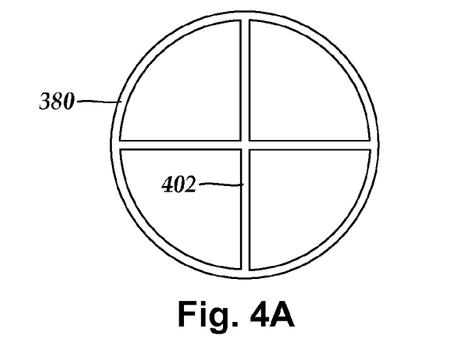
FIG. 4A is a schematic transverse cross-sectional view of one embodiment of an extension element of a lead body arrangement of the paddle lead assembly of FIG. 3C, according to the invention.
Figure 4B:
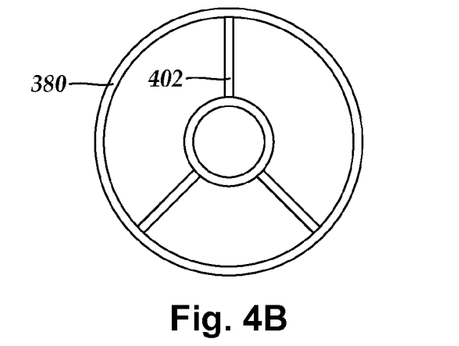
FIG. 4B is a schematic transverse cross-sectional view of one embodiment of an extension element of a lead body arrangement of the paddle lead assembly of FIG. 3C, according to the invention.
Figure 4C:
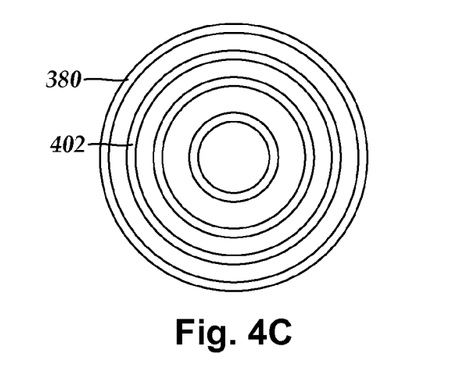
FIG. 4C is a schematic transverse cross-sectional view of one embodiment of an extension element of a lead body arrangement of the paddle lead assembly of FIG. 3C, according to the invention.

Conductive wires can be disposed in the extension element 380 in any configuration. It may be an advantage to extend conductive wires along the extension element 380 arranged into distinct (by sight, by touch, or the like) groupings that correspond to each of the plurality of lead bodies 382. In at least some embodiments, one or more dividers may extend along all, or a portion, of the extension element 380 to separate one or more of the groupings from one another. FIG. 4A is a schematic transverse cross-sectional view of one embodiment of an arrangement of dividers 402 disposed along the extension element 380. FIG. 4B is a schematic transverse cross-sectional view of a second embodiment of an arrangement of dividers 402 disposed along the extension element 380. FIG. 4C is a schematic transverse cross-sectional view of a third embodiment of an arrangement of dividers 402 disposed along the extension element 380.

The transverse profile of the extension element 380 can be any geometric or non-geometric shape including, for example, round, oval, rectangular, rounded rectangular, or the like. In preferred embodiments, the transverse profile of the extension element is formed so as to reduce patient discomfort. In at least some embodiments, the extension element 380 does not receive a stylet. In at least some embodiments, the extension element 380 does not couple directly to the one or more connectors 314.

Figure 5A:
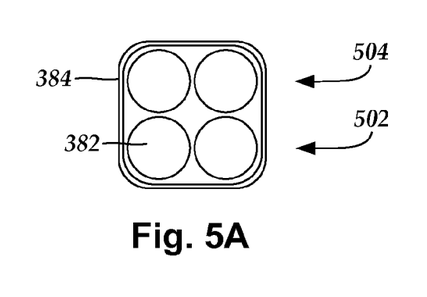
FIG. 5A is a schematic transverse cross-sectional view of one embodiment of a multi-layer arrangement of lead bodies disposed in a junction of the paddle lead assembly of FIG. 3C, according to the invention.

In at least some embodiments, the plurality of lead bodies 382 each couple to the junction 384 such that the lead bodies 382 are stacked into two or more layers. FIG. 5A is a schematic transverse cross-sectional view of one embodiment of the lead bodies 382 extending within the junction 384. The lead bodies 382 are arranged into two layers 502 and 504. It will be understood that the lead bodies 382 can be arranged into any number of layers, and each layer may include any number of lead bodies 382.

Figure 5B:
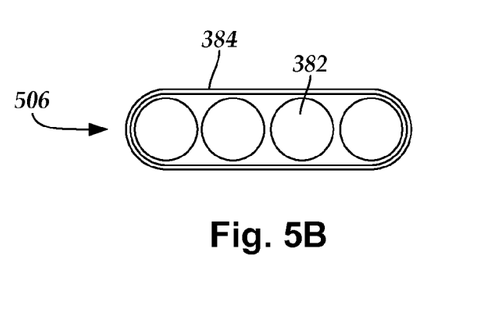
FIG. 5B is a schematic transverse cross-sectional view of another embodiment of a one-layer arrangement of lead bodies disposed in a junction of the paddle lead assembly of FIG. 3C, according to the invention.

In at least some embodiments, the lead bodies 382 couple to the junction 384 such that the lead bodies 382 are arranged into a single layer. FIG. 5B is a schematic transverse cross-sectional view of one embodiment of the lead bodies 382 extending within the junction 384. The lead bodies 382 are arranged into a single layer 506. It may be an advantage to couple the lead bodies 382 to the junction 384 in a single layer because a single layer of lead bodies 382 may produce less patient discomfort than multiple layers. It may also be an advantage to couple the lead bodies 382 to the junction 384 in a single layer because the arrangement of the lead bodies 382 may be configured in a manner that is similar to the arrangement of the electrodes 378, thereby facilitating identification of which lead body includes terminals coupled to which electrodes, or columns of electrodes.

Figure 6A:
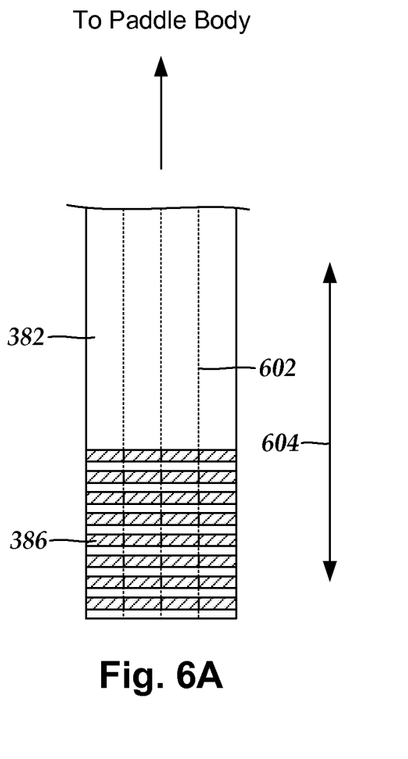
FIG. 6A is a schematic side view of one embodiment of proximal ends of lead bodies of a lead body arrangement, the lead bodies coupled together by perforated regions, according to the invention.
Figure 6B:
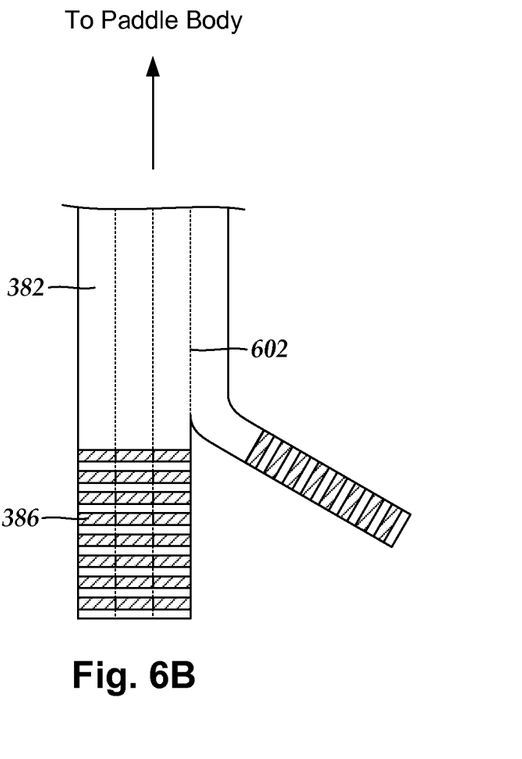
FIG. 6B is a schematic side view of one embodiment of proximal ends of the lead bodies of FIG. 6A, with one of the lead bodies separated from the other lead bodies due to separation along a perforated region, according to the invention.

Turning now to FIGS. 6A and 6B, in at least some embodiments the lead bodies 382 are at least partially coupled together along at least a portion of a longitudinal axis of the lead bodies 382. In at least some embodiments, the lead bodies 382 are coupled together such that one or more perforated regions (e.g., weakened regions, or the like) are formed along at least a portion of the coupled portions. In at least some embodiments, one or more of the lead bodies 382 can be separated from the other lead bodies 382 along one or more of the perforated regions and inserted into a connector.

FIG. 6A is a schematic side view of one embodiment of proximal ends of the lead bodies 382. The lead bodies 382 are arranged in a single layer such that the lead bodies 382 are in a side-by-side configuration. The lead bodies 382 are coupled together by one or more perforated regions, such as perforated region 602 extending along a longitudinal axis, shown in FIG. 6A as an arrow 604. In at least some embodiments, one or more of the perforated regions may be separated to partially detach one or more of the lead bodies 382 from one or more other of the lead bodies 382.

FIG. 6B is a schematic side view of one embodiment of proximal ends of the lead bodies 382. One of the perforated regions 602 has been separated along a proximal-most portion of the perforated region to partially separate one of the lead bodies 382 from the other lead bodies 382. In at least some embodiments, the separated lead body 382 can be inserted into a connector (e.g. of a control module, a lead extension, or the like). In at least some embodiments, the one or more perforated regions 602 can be separated by a medical practitioner during implantation of the electrical stimulation system 370. In at least some embodiments, the one or more perforated regions 602 can be separated after the paddle lead assembly 372 is inserted into a patient.

Figure 7:
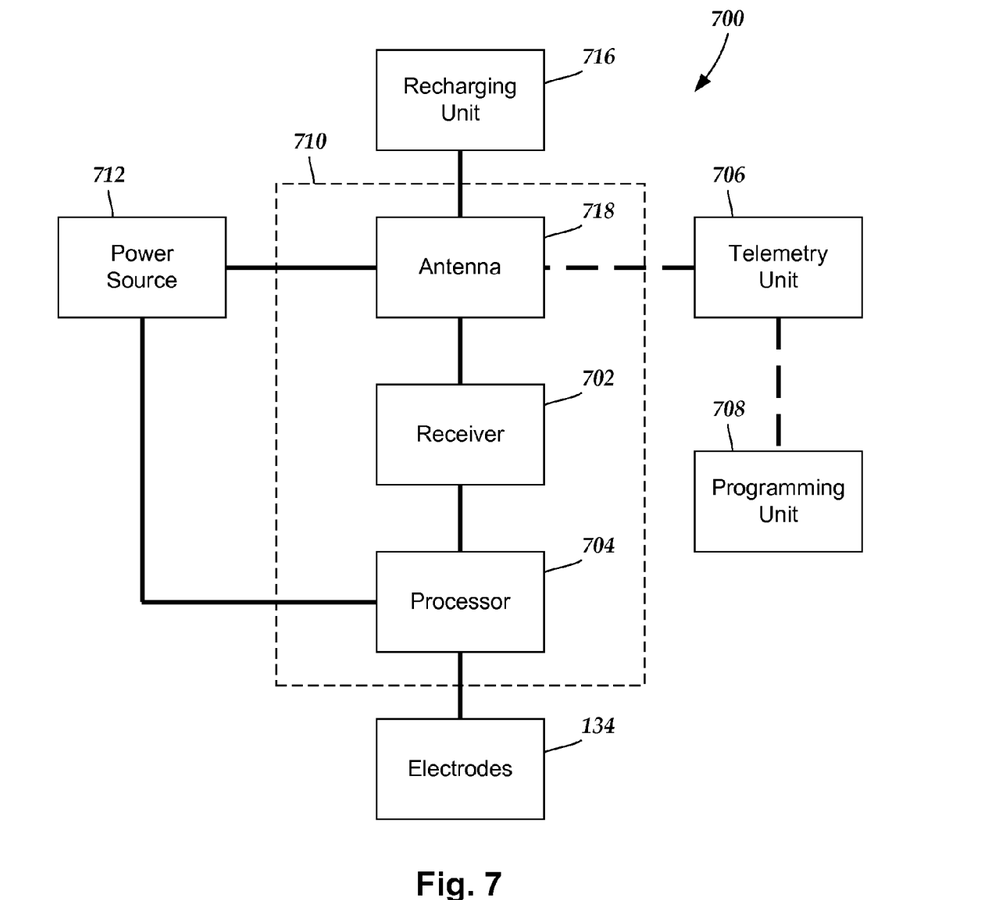
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, power source 712, antenna 718, receiver 702, and processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 may select which electrode(s) are cathodes and which electrode(s) are anodes. In some embodiments, the processor 704 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by a programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 1508 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include an antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A paddle lead assembly for providing electrical stimulation of patient tissue, the lead comprising:
   a paddle body comprising four columns of electrodes, wherein each of the four columns comprises a plurality of electrodes, wherein the four columns of electrodes includes two outer columns flanking two inner columns;
   at least one elongated extension element having a first end and an opposing second end, the first end of the at least one extension element coupled directly to the paddle body;
   a plurality of lead bodies coupled to the second end of the least one extension element, wherein the number of lead bodies is equal to the number of columns of electrodes;
   a different plurality of terminals disposed on each lead body of the plurality of lead bodies;
   a plurality of conductive wires electrically coupling each of the electrodes to at least one of the plurality of terminals;
   wherein for each of the different pluralities of terminals, the terminals are electrically coupled to a different column of electrodes of the four columns of electrodes than the terminals of the remaining different pluralities of terminals.

2. The paddle lead assembly of claim 1, further comprising a junction disposed at the second end of the at least one extension element, the junction coupling the at least one extension element to each of the plurality of lead bodies, wherein the plurality of conductive wires extend along the at least one extension element to the junction, wherein the plurality of conductive wires are divided up into a plurality of distinct groupings in the junction, and wherein a different one of the groupings of conductive wires extends along each of the plurality of lead bodies.

3. The paddle lead assembly of claim 2, wherein the plurality of lead bodies couple to the junction such that the plurality of lead bodies are stacked into a plurality of layers, each layer comprising at least two lead bodies.

4. The paddle lead assembly of claim 2, wherein the plurality of lead bodies couple to the junction such that the plurality of lead bodies are arranged into a single layer in a side-by-side configuration that comprises at least one inner lead body flanked by two outer lead bodies.

5. The paddle lead assembly of claim 4, wherein the at least one electrode of each of the outer columns is electrically coupled to the at least one terminal disposed on the two outer lead bodies and the at least one electrodes of each of the inner columns is electrically coupled to the at least one terminal disposed on each of the two inner lead bodies.

6. The paddle lead assembly of claim 4, wherein each of the plurality of lead bodies is coupled to at least one adjacent lead body by at least one weakened region configured and arranged to permit manual separation of the coupled lead bodies.

7. The paddle lead assembly of claim 6, wherein the conductive wires extending along the extension element are divided into distinct groupings of conductive wires, and wherein a number of distinctive groupings is equal to a number of different columns of electrodes.

8. The paddle lead assembly of claim 2, wherein each distinct grouping of conductive wires extending along the extension element is separated from the other distinct groupings of conductive wires by one or more dividers extending along a length of the extension element.

9. The paddle lead assembly of claim 1, further comprising at least one lead splitter.

10. The paddle lead assembly of claim 9, wherein the at least one lead splitter comprises a splitter connector and at least two splitter lead bodies, and wherein the splitter connector is configured and arranged to receive at least one of the plurality of lead bodies.

11. The paddle lead assembly of claim 1, wherein each of the four columns of electrodes comprises eight electrodes and each of the plurality of lead bodies comprises eight terminals.

12. The paddle lead assembly of claim 11, wherein for each of the four columns of electrodes the electrodes are coupled to the terminals of one of the plurality of lead bodies such that a proximal-most electrode is electrically coupled to a proximal-most terminal and a distal-most electrode is electrically coupled to a distal-most terminal.

13. The paddle lead assembly of claim 11, wherein for each of the four columns of electrodes the electrodes are coupled to the terminals of one of the plurality of lead bodies such that a proximal-most electrode is electrically coupled to a distal-most terminal and a distal-most electrode is electrically coupled to a proximal-most terminal.

14. The paddle lead assembly of claim 1, wherein the plurality of lead bodies each has a different length.

15. The paddle lead assembly of claim 1, wherein at least one distinct marker is disposed on or in at least one of the plurality of lead bodies.

16. An electrical stimulating system comprising:
the paddle lead assembly of claim 1;
at least one control module configured and arranged to electrically couple to each of the plurality of lead bodies, each of the at least one control module comprising
a housing, and
an electronic subassembly disposed in the housing; and
a connector configured and arranged for receiving at least one of the plurality of lead bodies, the connector comprising
a connector housing defining at least one port at a distal end of the connector, the at least one port configured and arranged for receiving a portion of at least one of the plurality of lead bodies, and
at least one connector contact disposed in each of the at least one ports defined by the connector housing, the at least one connector contact configured and arranged to couple to the at least terminal disposed on each of the plurality of the lead bodies.

17. The electrical stimulating system of claim 16, further comprising at least one lead extension coupling each of the plurality of lead bodies to the at least one control module.

18. A method for implanting a paddle lead, the method comprising:
inserting the paddle lead assembly of claim 6 into a patient,
separating the weakened region between a first proximal element and an adjacent second proximal element such that the terminals of the first proximal element are separated from terminals disposed on the second proximal element; and
inserting the terminals of the first proximal element into a connector electrically coupled to an implantable pulse generator.

* * * * *